United States Patent [19]

Ramachandran et al.

[11] Patent Number: 5,693,856
[45] Date of Patent: Dec. 2, 1997

[54] PRODUCTION OF TEREPHTHALIC ACID

[75] Inventors: Ramakrishnan Ramachandran, Allendale; Rustam H. Sethna, New Brunswick; Satish S. Tamhankar, Scotch Plains, all of N.J.

[73] Assignee: The BOC Group, Inc.

[21] Appl. No.: 587,174

[22] Filed: Jan. 16, 1996

[51] Int. Cl.$^6$ .................................................. C07C 51/16
[52] U.S. Cl. ............................................................ 562/414
[58] Field of Search ..................................... 562/412, 413, 562/414

[56] References Cited

U.S. PATENT DOCUMENTS

| | | | |
|---|---|---|---|
| 4,172,209 | 10/1979 | Vora | 562/414 |
| 4,263,448 | 4/1981 | Leacock | 560/246 |
| 4,593,122 | 6/1986 | Hashizume et al. | 562/414 |

*Primary Examiner*—Samuel Barts
*Attorney, Agent, or Firm*—Coleman R. Reap; Salvatore P. Pace

[57] ABSTRACT

Terephthalic acid is produced by reacting paraxylene with oxygen in a reactor having several vertical stages, the reaction taking place in the liquid phase using acetic acid as solvent and a cobalt-manganese-bromine complex catalyst. During the reaction, a carbon dioxide-containing gas phase is withdrawn from the vapor space of the reactor. The gas phase is cooled to condense vaporized acetic acid therefrom and carbon dioxide is separated from the gas phase and recycled to the vapor space or to the liquid phase or to both of these. In an alternate embodiment, the gas remaining after condensing acetic acid is subjected to catalytic oxidation to oxidize carbon monoxide and methane, if present, to carbon dioxide, and some or all of the carbon dioxide is recycled to the reactor.

19 Claims, 2 Drawing Sheets

PRODUCTION OF TEREPHTHALIC ACID

FIELD OF THE INVENTION

This invention relates to the manufacture of aromatic polyacids and more particularly to the manufacture of phthalic acids by a liquid phase process in which carbon dioxide is separated from the gaseous effluent and recycled to the reaction zone.

BACKGROUND OF THE INVENTION

Aromatic polyacids are widely used as intermediates in chemical manufacture. For example, terephthalic acid (TPA), a building block in the production of polyester polymers, is generally commercially produced by the liquid phase partial oxidation of paraxylene (p-xylene) with an oxygen-containing gas using an aliphatic acid, such as glacial acetic acid, as the solvent, and a catalyst which is highly selective for the production of terephthalic acid. The reaction can be carried out in a stirred single stage or multiple vertical stage reactor at a temperature in the range of about 170° to 225° C. and a pressure of about 100 to 300 psig (pounds per square inch gauge). P-xylene and the acid solvent are continuously introduced at the top of the reactor and oxygen-containing gas is preferably introduced into the lowest stage or into each stage. The oxygen dissolves in the solvent and reacts with paraxylene to form terephthalic acid and various byproducts, such as 4-carboxybenzaldehyde (4-CBA). These products are continuously withdrawn at or near the bottom of the reactor. Carbon oxides are also formed by over oxidation of the p-xylene and oxidation of the acetic acid solvent. These products rise to the top of the reactor and are continuously withdrawn from the reactor. Typical aromatic acid manufacturing processes are described in U.S. Pat. Nos. 4,329,493; 4,593,122; 4,827,025; 4,835,307; and 5,087,741.

Two principal problems are associated with the above-described process. The reactions are usually carried out in the presence of a stoichiometric excess of oxygen. As noted above, carbon monoxide is produced as a byproduct of the reaction. In addition, gaseous hydrocarbon derivative byproducts, such as methyl acetate are formed during the reaction, and since the reaction is carried out at high temperatures, acetic acid is volatilized, in spite of the fact that the reaction is carried out at relatively high pressures. Accordingly, the vapor phase contains significant quantities of these compounds. It can readily be appreciated that there is a considerable potential for the formation of a flammable gas mixture in the vapor space of the reactor and in the lines and equipment that are used to treat the gas phase. The problem is aggravated by the fact that the reaction is carried out at relatively high temperatures, which widens the range of gas mixtures that fall within the flammable gas envelope. Furthermore, more efficient aromatic acid manufacturing processes have been developed which use oxygen-enriched air or high purity oxygen as the oxidant. These processes are even more susceptible to formation of flammable gas mixtures in the vapor space, since the diluent effect provided by nitrogen when air is used in the reaction is not available when high purity oxygen is used as the oxidant.

U.S. Pat. No. 5,371,283 discloses a method of reducing the flammability of gas in the vapor space of a terephthalic acid manufacturing reactor in which oxygen is used as the oxidant by designing the reactor so that there is no interface between the gas phase and the liquid phase in the reactor, and by passing an inert gas, such as nitrogen through the vapor space during the reaction. Although this patent discloses a technique for reducing the hazard of flammability in a terephthalic acid manufacturing process, it is readily apparent that the reactor design disclosed in this patent is complex and that nitrogen must be imported into the system.

Processes which are highly efficient and have a reduced risk of flammability or explosion hazard are continually sought. The present invention discloses a carbon dioxide recycle process which achieves this goal and which also reduces the amount of acetic acid solvent that is lost in the overhead gas removal step.

SUMMARY OF THE INVENTION

According to the invention, an aromatic polycarboxylic acid is produced by reacting a polyalkyl benzene compound with oxygen in the presence of a catalyst which effects the partial oxidation of the polyalkyl benzene compound to the aromatic polycarboxylic acid. The reaction is carried out in the liquid phase using a lower aliphatic acid as solvent at a temperature in the range of about 150° to about 250° C. and at a pressure sufficiently high to maintain the liquid phase.

A waste gas stream containing carbon dioxide and carbon monoxide is removed from the vapor space in the uppermost region of the reactor. A carbon dioxide-enriched gas formed from the waste gas stream is recycled to the reactor. The carbon dioxide-enriched gas can be recycled to the vapor space, to the liquid phase or to both of these.

In a preferred embodiment the carbon dioxide-enriched gas is at least partly formed by condensing lower aliphatic acid from the waste gas stream.

The process of the invention is ideally suited to the preparation of orthophthalic acid, isophthalic acid or terephthalic acid by the oxidation of ortho-, meta- and paraxylene, respectively. In the most preferred embodiment of the invention, terephthalic acid is produced by the liquid phase oxidation of paraxylene using acetic acid as the solvent.

According to one embodiment, the carbon dioxide-rich gas stream is at least partly formed by removing part of the carbon dioxide from the waste gas. The carbon dioxide is preferably removed from the gas stream by absorption or adsorption.

According to an alternate embodiment, the carbon dioxide-rich gas stream is at least partly formed by oxidizing carbon monoxide and hydrocarbon, if present, in the waste gas to carbon dioxide.

In a preferred embodiment, the reactor in which the partial oxidation of the polyalkyl benzene compound takes place comprises two or more liquid phase reaction zones arranged in vertical stages. Oxygen-rich gas is introduced into the lowermost stage, and in a preferred embodiment it is also introduced into one or more of the other vertical stages in the reactor. The carbon dioxide-rich gas can be introduced into the vapor space above the liquid phase in the reactor and/or into any one or more than one of the vertical stages. In a preferred embodiment, the carbon dioxide is introduced into the vapor space and into one or more vertical stages in the upper part of the reactor.

BRIEF DESCRIPTION OF THE DRAWINGS

Where applicable, the same reference numerals are used to represent the same or similar parts in the various drawings.

DETAILED DESCRIPTION OF THE INVENTION

Figure 1:
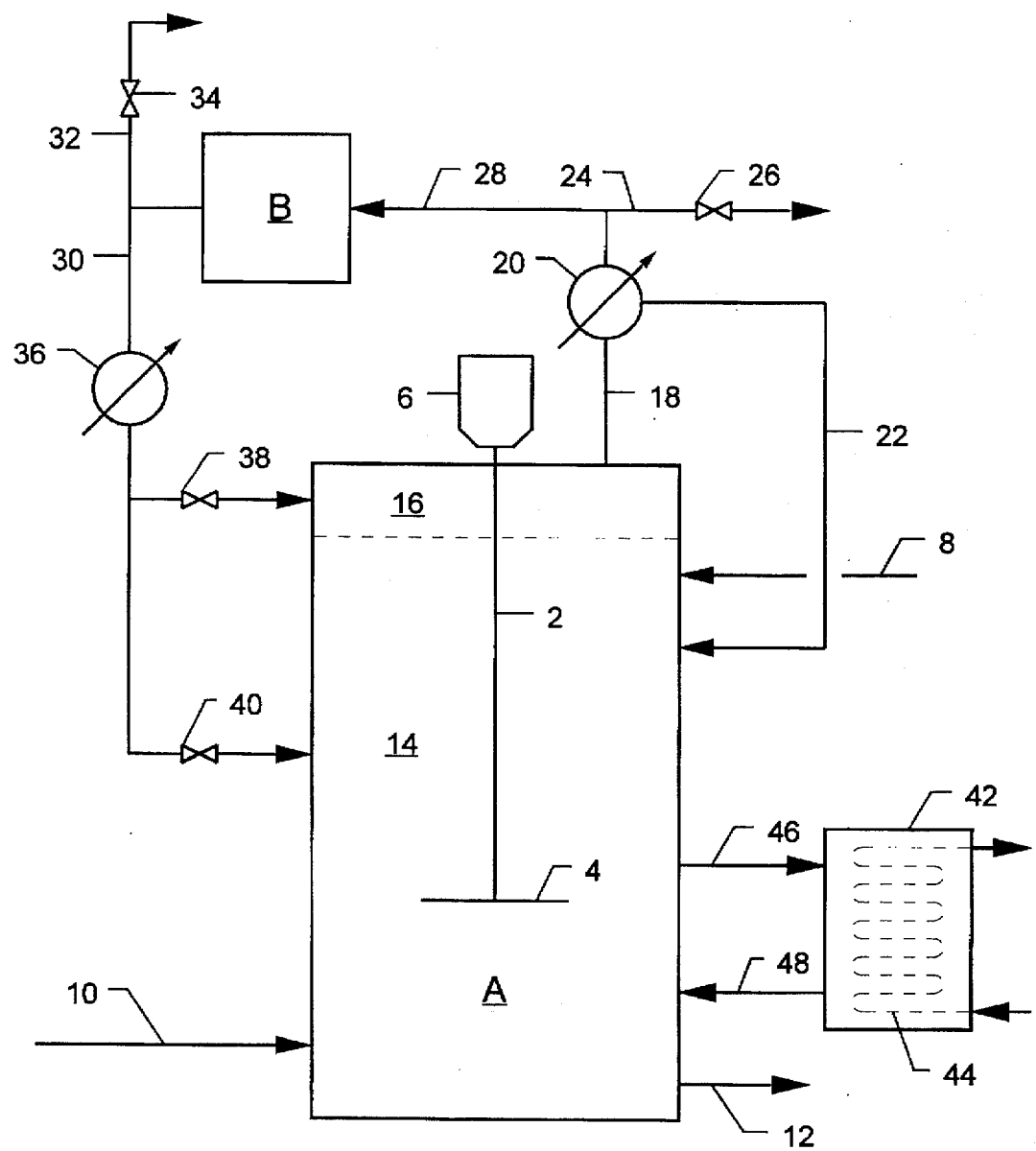
FIG. 1 is a schematic drawing illustrating an embodiment of the invention in which the partial oxidation reaction of the polyalkyl benzene compound is carried out in a single stage reactor.

The invention comprises carrying out the liquid phase partial oxidation of a polyalkyl-substituted benzene to produce an aromatic polycarboxylic acid in a manner that provides better control of the temperature in the reaction vessel during the reaction and reduces losses of the polyalkyl-substituted benzene and the aliphatic acid occurring during the reaction. The production of aromatic polycarboxylic acids by the process discussed in this specification forms no part of the invention, and the reaction conditions, i.e. reaction temperature and pressure and ratio of the reactants and the particular reactants, catalyst and solvent used in the invention forms no part of the invention.

The invention comprises separating carbon dioxide from the gas phase formed during the oxidation reaction and recycling the carbon dioxide to the reaction vessel. The recycled carbon dioxide serves as a heat transfer agent and improves distribution of the heat generated during the reaction, which is exothermic. The carbon dioxide also serves as a diluent of the gas in the vapor space and prevents formation of a flammable mixture in the vapor space and the downstream equipment and lines. To accomplish these objectives the separated carbon dioxide can be recycled to either or both of the liquid phase or the vapor space above the liquid phase. The separation and distribution of the carbon dioxide is discussed in more detail below.

The polyalkyl benzene compounds that are useable as reactants in the process of the invention include, in particular, the dimethyl benzenes, i.e. orthoxyxlene, metaxylene, and paraxylene, and the trimethyl benzene compounds, such as mesitylene, etc. Aromatic polycarboxylic acids that can be produced by the process of the invention include orthophthalic acid, isophthalic acid and terephthalic acid, produced from ortho-, meta- and paraxylene, respectively, and the benzene tricarboxylic acids.

The oxidation of the polyalkyl benzene compounds is accomplished by reacting these compounds with an oxygen-rich gas. For purposes of this invention an "oxygen-rich gas" is defined as substantially pure oxygen or an oxygen-inert gas mixture containing at least 80 volume percent oxygen. In preferred embodiments of the invention, the oxygen-rich gas contains at least 90 volume percent oxygen, and in the most preferred embodiment, the oxygen-rich gas is substantially pure oxygen. An "inert gas" is a gas that will not react with any of the components of the reaction mixture under the conditions at which the oxidation reaction is carried out. Typical inert gases include nitrogen, argon and carbon dioxide.

The oxidation reaction is carried out in the liquid phase using an lower aliphatic acid as solvent. Preferred lower aliphatic acids are those having up to about six carbon atoms, such as acetic acid, propionic acid, the butyric acids, the pentanoic acids and the hexanoic acids. The lower aliphatic acid may be substantially pure acid or it may be in the form of an aqueous solution. Acetic acid, particularly glacial acetic acid, is the preferred solvent for use in the invention.

The catalyst used in the process of the invention comprises one or more heavy metal compounds, preferably with a bromine compound. Heavy metal compounds include salts and organic complexes of cobalt, iron, chromium, manganese, etc. Typical compounds of this group include, cobalt acetate, manganese naphthenate, manganese bromide, nickel bromide, chromium bromide, iron acetate, nickel acetate, chromium acetate, etc. In addition to the bromide compounds mentioned above, other bromides, such as tetrabromoethane, can be used in the process. The most preferred catalyst is a combination of cobalt compound, a manganese compound and a bromine-containing compound.

The invention can be better understood from the accompanying drawings. Auxiliary equipment, including valves, compressors and heat exchangers, that is unnecessary for an understanding of the invention have been omitted from the drawings to simplify discussion of the invention.

Illustrated in FIG. 1 is a system for producing aromatic polycarboxylic acids by the process of the invention which includes, as major equipment components, reaction vessel A and carbon monoxide oxidizer B. The apparatus of FIG. 1 is adapted for the continuous flow of reactants into, and the continuous withdrawal of aromatic polyacid product from, the reaction vessel. Reactor A can be constructed of any material suitable for carrying out the reaction, such as carbon steel, stainless steel, etc. If desired this vessel can be glass lined. Suitable reaction vessels are well known and their design and construction form no part of this invention. Reactor A is provided with stirrer shaft 2, which has one or more agitator blades 4. Shaft 2 is driven by any suitable means, such as electric motor 6. Reactor A is also provided with solvent and polyalkyl benzene feed line 8, oxygen-rich gas feed line 10 and aromatic polycarboxylic acid product removal line 12. In the embodiment illustrated in FIG. 1, reactor A contains a liquid phase, 14, of any desired volume, and above the liquid phase, a vapor space, 16. Located at or near the top of reactor A is vapor gas discharge line 18, which is connected to the inlet end of condenser 20. Condensate line 22 provides for the return of condensed acid solvent to reactor A. Waste gas vent line 24, fitted with valve 26 connects the outlet of condenser 20 to a downstream waste gas treatment facility or to an atmospheric vent. Carbon dioxide gas recycle line 28 connects line 24 at a point upstream of valve 26 with the inlet end of oxidizer B.

Oxidizer B can be any device that serves to oxidize carbon monoxide and any light hydrocarbons contained in the waste gas to carbon dioxide. Preferably, oxidizer B is a catalytic reactor which contains one or more catalysts which cause the oxidation of carbon monoxide, methane, etc to carbon dioxide and water vapor in the presence or absence of oxygen. Oxidizer B and line 32 can be eliminated from the system of FIG. 1, if desired, in which case carbon monoxide and excess carbon dioxide are removed from the system through line 24.

On its outlet end, oxidizer B is provided with carbon dioxide recycle line 30, which is connected to optional gas vent 32, fitted with valve 34, and to the inlet of carbon dioxide chiller 36. Carbon dioxide chiller 36 can be any suitable heat exchange device that can chill the carbon dioxide to the desired temperature. When the oxygen-rich gas used in the process of the invention is oxygen product from a cryogenic air separation unit (ASU), the carbon dioxide-rich gas is typically chilled by first heat exchanging it with cooling water and then further chilling it by heat exchange with cold oxygen-rich gas from the ASU. This serves the dual purpose of chilling the carbon dioxide-rich gas and heating the oxygen-rich gas prior to their introduction into reactor A. The outlet end of chiller 36 is connected to both the vapor space and the liquid phase space of reactor A. Valve 38 controls flow of carbon dioxide-rich gas to the vapor space, and valve 40 controls flow of carbon dioxide-rich gas to the liquid phase space.

Reactor A is also equipped with liquid phase cooler 42, which, in the embodiments illustrated in the drawings, removes heat from the reacting mixture by indirect contact of the reaction mixture with cooling water. The cooling water passes through coil 44, and as it does so it is heated. Hot water or steam exits cooler 42 through coil 44 at or near the upper end of cooler 42. Liquid phase is drawn from reactor A to cooler 42 through line 46 and is returned to reactor A through line 48. Other means of cooling the reaction medium in reactor A can be used instead of, or in combination with cooler 42, if desired.

For ease of discussion, the process of the invention will be described in detail as it applies to the production of terephthalic acid by the reaction of p-xylene with oxygen-rich gas in glacial acetic acid using a cobalt-manganese-bromide catalyst combination, although the invention is equally applicable to the production of other aromatic polyacids with oxygen-containing gas using other aliphatic acids as solvents and using other catalysts that are suitable for the desired reaction.

In practicing the invention in the apparatus illustrated in FIG. 1, reactor A is filled via line 8 with a mixture of p-xylene, acetic acid and cobalt-manganese-bromide catalyst mixture, such as cobalt acetate, manganese acetate and hydrobromic acid, to the desired level, indicated in FIG. 1 by the dashed line. These components can be introduced separately into reactor A through separate feed lines, or they can be combined and introduced into reactor A, as shown in FIG. 1. Oxygen-rich gas is introduced into reactor A through line 10. Partial oxidation of the p-xylene takes place upon contact of the reactants and catalyst. The reactor contents are continuously stirred during the reaction by rotation of agitator blade(s) 4, driven by means of shaft 2 and motor 6. The reaction, which is exothermic, causes the temperature of the liquid phase to rise. The temperature of the liquid phase is maintained in the range of about 150° to about 200° C., and preferably in the range of about 150° to about 170° C., by circulation of the reaction medium through cooler 42, and by introduction of cooled carbon dioxide into reactor A through valves 38 and 40. To reduce the possibility of forming a flammable gas mixture in vapor space 16 during the startup period of the process, which begins upon startup and generally continues until steady state conditions are attained, it may be desirable to use air as the oxidant until sufficient carbon dioxide is generated and recycled to maintain the gas in vapor space 16 nonflammable. Alternatively, it may be preferred to start the process initially with oxygen-rich gas and import carbon dioxide into the system from an outside source during the startup period.

As the reaction proceeds, terephthalic acid is produced, and this product, together with part of the reactants and solvent, is continuously withdrawn from reactor A through line 12. The terephthalic acid is separated from the reactants and solvent downstream of line 12, and the reactants and solvent can be subsequently returned to reactor A via line 8, if desired. Make-up reactants necessary to maintain the desired liquid phase level in reactor A are likewise provided through line 8.

During the course of the reaction, gaseous products, including carbon monoxide, carbon dioxide, acetic acid vapor and various byproducts gather in vapor space 16. The gas components are continuously discharged from the vapor space of reactor A through line 18. The hot gas passes through condenser 20 wherein it is cooled sufficiently to condense substantially all of the acetic acid perhaps some or all of the water vapor contained in the gas. The condensed acetic acid and water vapor are recycled to reactor A through line 22. The remaining gas then passes out of condenser 20 through line 24 and next enters oxidizer B. If desired a portion of the gas can be vented through the system through line 24 by opening valve 26. Carbon monoxide and any hydrocarbons or other byproducts present in the gas entering oxidizer B are converted therein to carbon dioxide upon contact with the catalyst contained in oxidizer B. The carbon dioxide-rich gas stream, now comprised substantially of carbon dioxide and perhaps nitrogen, if oxygen-enriched air is used as the oxidant, exits oxidizer B through line 30. At this point a part of the carbon dioxide gas can be discharged from the system through line 32, if desired, by opening valve 34. The carbon dioxide-rich gas to be recycled to reactor A is next preferably pressurized and refrigerated, for example to a temperature of about 25° to abut 100° C. by passage through heat exchanger 36. As noted above, refrigeration for the carbon dioxide can be provided by passing oxygen obtained from a cryogenic air separation unit through heat exchanger 36.

The chilled carbon dioxide-rich gas from chiller 36 can be introduced into either or both of the liquid phase or the vapor space in reactor A. It is generally desirable to introduce part of the carbon dioxide-rich gas into the liquid phase and the remainder into the vapor space. This provides multiple advantages. Firstly, it facilitates maintenance of a more uniform temperature in the liquid phase, and secondly, it ensures that a flammable mixture does not form in the vapor space by both diluting and cooling the gas phase. When carbon dioxide is introduced into the liquid phase, it is preferred to introduce it into the upper region of the liquid phase, since this cools the upper part of the liquid phase, thereby reducing the amount of the acetic acid which vaporizes. An advantage of introducing the carbon dioxide into the upper part but not the lower part of the liquid phase in reactor A is that the lower part of the liquid phase can be maintained at a higher temperature, which enhances the selectivity of the partial oxidation reaction for the production of terephthalic acid rather than undesirable byproducts, such as 4-carboxybenzaldehyde (4-CBA). In a less preferred alternative, the chilled carbon dioxide can be combined with the oxygen and the mixture jointly introduced into reactor A.

Figure 2:
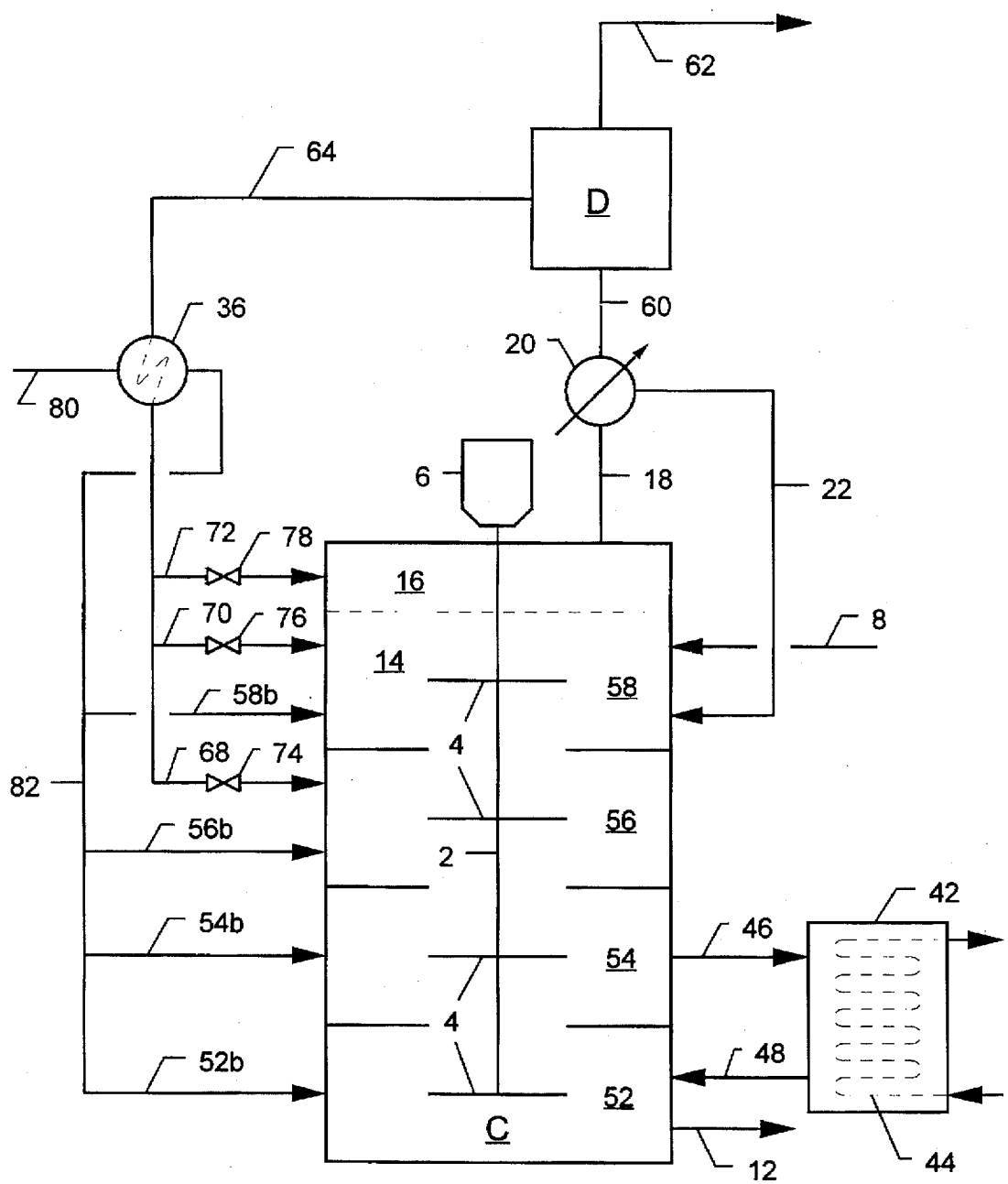
FIG. 2 is a schematic drawing illustrating an alternate embodiment of the invention in which the partial oxidation reaction is carried out in a multiple stage reactor.

FIG. 2 illustrates apparatus for carrying out a more preferred embodiment of the invention. The principal apparatus components in this embodiment are multiple stage reactor C and carbon dioxide separator D. Reactor C contains four liquid phase reaction zones, zones 52, 54, 56 and 58, which are arranged in vertical array. Agitator blades 4, driven by shaft 2, provide stirring of the liquid phase in each of the reaction zones. Reactor C is provided with oxidant gas feed lines 52b, 54b, 56b, and 58b, which introduce oxygen-rich gas into the respective reaction zones.

In the FIG. 2 embodiment, the outlet end of condenser 20 is connected to the inlet end of separator D via line 60. Separator D may be any means capable of separating carbon dioxide from the gas stream exiting condenser 20, but is preferably a liquid absorption plant containing a solvent which selectively absorbs carbon dioxide from the reactor C waste gas stream, or an adsorption plant which contains an adsorbent which selective adsorbs carbon dioxide from the waste gas. When separator D is an absorption plant, it preferably contains an alkanolamine, such as ethanolamine or diethanolamine, and when it is an adsorption plant it preferably contains a natural zeolite, such as faujasite, mordenite, etc., or a synthetic zeolite, such as type X or type A zeolite. These absorbents and adsorbents will selectively sorb carbon dioxide from the waste gas stream. Alternatively, an adsorbent that selectively adsorbs components other than carbon dioxide can be used to separate the carbon dioxide from the other components of the waste gas stream. It is preferable that separator C comprise a plurality of sorption units that can be operated out of phase, such that one unit is in carbon dioxide sorption service while the other unit is being regenerated. If desired, separator D can be eliminated from the system of FIG. 2, in which case carbon monoxide and excess carbon dioxide are removed from the system through line 62.

Separator D is provided with vent gas outlet line 62 which is connected to a downstream waste gas disposal unit, and carbon dioxide recycle line 64. The waste gas treatment section of FIG. 2 may also be provided with an oxidizer, such as oxidizer B of FIG. 1, if desired. When an oxidizer is used it can be positioned in line 60 or in line 64. If the oxidizer is placed in line 60, the waste gas stream in line 62 will be substantially free of environmentally objectional gas components and accordingly, can be discharged directly to the atmosphere. On the other hand, when an oxidizer is placed in line 64, it can be a much smaller unit, since the volume of oxidizable gases in line 64 is considerably lower than the volume of these gases in line 60. With proper absorbent or adsorbent selection, the carbon dioxide recycle gas in line 64 will contain little or no oxidizable gas.

In the embodiment illustrated in FIG. 2, line 64 passes through heat exchanger 36 and, on the downstream side of heat exchanger 36, line 64 is connected to lines 68, 70 and 72, which are, in turn, connected to reaction zones 58 and 56 and vapor space 16, respectively. Flow of gas through lines 68, 70 and 72 is controlled by valves 74, 76 and 78, respectively. Oxygen-rich gas supply line 80 passes through heat exchanger 36 in indirect heat exchange relationship with the carbon dioxide gas flowing through line 64. Downstream of heat exchanger 66, line 80 is connected to manifold 82, which in turn is connected to lines 52b, 54b, 56b and 58b. Also, as shown in FIG. 2, lines 46 and 48 are respectively connected to reaction zones 54 and 52.

In practicing the invention in the apparatus illustrated in FIG. 2, reactor C is filled with a mixture of p-xylene, acetic acid and cobalt-manganese-bromide catalyst mixture, such as cobalt acetate, manganese acetate and hydrobromic acid, to the desired level, indicated in FIG. 2 by the dashed line. The liquid phase is then heated to a temperature in the range of about 150° to about 200° C., and preferably to a temperature in the range of about 150° to about 170° C., and with continuous stirring in each reaction zone, oxygen-rich gas is introduced into each of the four reaction zones through lines 52b, 54b, 56b and 58b. In the illustrated embodiment, the oxygen-rich gas is produced in a cryogenic air separation unit and supplied to heat exchanger 36 at very low temperatures. Where a cryogenic air separation unit is not available or not desired, the oxygen-rich gas can be provided by other means such as, for example, an adsorptive air separation plant. In such case, the carbon dioxide-rich gas in line 64 will be cooled by other means, such as by refrigeration.

As the reaction proceeds, gaseous products gather in vapor space 16 and are continuously discharged from the vapor space of reactor C through line 18. The hot gas passes through condenser 20 wherein it is cooled sufficiently to condense substantially all of the acetic acid and perhaps some or all of the water vapor contained in the gas. The condensed acetic acid and water vapor are recycled to reactor C through line 22. The remaining gas passes out of condenser 20 through line 60 and next enters separator D. It may be desirable to include at the inlet end of separator D a gas dryer, such as one or more beds of silica gel or activated alumina desiccant, to remove substantially all of the water vapor from the waste gas. This is usually desirable when separator D contains an adsorbent, since most adsorbents preferentially adsorb water vapor relative to carbon dioxide and other gases. Alternatively, a hydrophobic adsorbent can be used for the carbon dioxide separation. The carbon dioxide-rich gas stream, now comprised substantially of carbon dioxide, exits separator D through line 64, and the other gas components of the waste gas exit the system through line 62. The carbon dioxide-rich gas is refrigerated, preferably to a temperature in the range of about 25° to about 100° C. by passage through heat exchanger 36. The refrigerated carbon dioxide is then introduced into vapor space 36 and/or one or both of reaction zones 56 and 58 and/or into vapor space 16 by means of valves 74, 76 and 78, respectively.

During the course of the reaction, the liquid reactant mixture passes downwardly through the various reaction zones. In the FIG. 2 embodiment, liquid phase is withdrawn from reaction zone 54, cooled in cooler 42 and returned to reaction zone 52, which maintains the reaction temperature in the lower region of reactor C at the desired level. As the temperature of the reaction mixture rises, the partial oxidation reaction becomes more selective, with the result that very little or no 4-CBA is produced as a byproduct. Thus the purity of the terephthalic acid product exiting reactor C through line 12 is very high.

The process practiced in the system of FIG. 2 is continuous and the make-up reactants necessary to maintain the desired liquid phase level in reactor A are provided through line 8.

It will be appreciated that it is within the scope of the present invention to utilize conventional equipment to monitor and automatically regulate the flow of liquids and gases within the system so that it can be fully automated to run continuously in an efficient manner.

The invention is further illustrated by the following example in which, unless otherwise indicated, parts, percentages and ratios are on a volume basis.

EXAMPLE 1

A commercial scale continuous terephthalic acid production run was simulated in a liquid phase reactor system similar to the system of FIG. 2, except that separator D was eliminated and part of the waste gas stream in line 60 was recycled to reactor C via line 64 and the remainder was removed from the system through line 62. The reaction was simulated based on the following assumptions: All of the oxidant (commercially pure oxygen) is introduced into reactor C through line 52b; 85% by volume of the waste gas stream leaving separator D is recycled to reactor C and the remainder is removed from the system; 90% by volume of the recycled carbon dioxide-rich stream is introduced into the vapor space of reactor C through line 72 and the remainder is introduced into the liquid phase through line 76; the pressure in reactor C was maintained at 200 psig during the run; and sufficient cooling was provided by heat exchangers 36 and 42 to maintain the temperature at the top and bottom of reactor C at 160° and 180° C., respectively. The various flow rates in kg/hr and projected results are tabulated in the TABLE. The numerals in parentheses refer to pipelines in FIG. 2.

TABLE

| Component | Feed (8) | Product (12) | Reflux (18) | Ovhd[1] (60) | Recycle (64) | Vent (62) |
|---|---|---|---|---|---|---|
| Water | 10,839 | 21,366 | 39,092 | 100 | 85 | 15 |
| Acetic Acid | 43,354 | 41,939 | 178,033 | 115 | 98 | 17 |
| p-Xylene | 21,075 | 205 | 26,058 | 7 | 6 | 1 |
| Catalyst[2] | 223 | 223 | | | | |
| TPA[3] | | 31,692 | | | | |
| MA[4] | | 967 | | 415 | 53 | 62 |
| Oxygen | 21,612 | | | | | |
| $CO_2$ | | | | 1,336 | 1,136 | 200 |

[1]overhead vapor stream
[2]cobalt acetate-manganese acetate-hydrobromic acid combination
[3]terephthalic acid
[4]methyl acetate The above example illustrates a general embodiment of the invention. The selectivity to terephthalic acid is projected to be 97%, and the acetic acid lost from the system is 3% by volume.

Although the invention has been described with particular reference to specific equipment arrangements and to specific experiments, these features are merely exemplary of the invention and variations are contemplated. For example, vertical or horizontal vessels can be used in any of the embodiments of the invention. The scope of the invention is limited only by the breadth of the appended claims.

What is claimed is:

1. A process for the manufacture of aromatic polycarboxylic acids comprising
   (a) contacting, in the liquid phase in a reactor partially filled with a saturated aliphatic acid as solvent, a polyalkyl-substituted benzene and an oxygen-rich gas in the presence of a heavy metal partial oxidation catalyst which selectively oxidizes the polyalkyl-substituted benzene to an aromatic polycarboxylic acid, thereby producing a liquid product comprising said aromatic polycarboxylic acid and a condensable vapor-containing waste gas stream comprising carbon dioxide;
   (b) separating condensable vapors from said waste gas stream;
   (c) forming a carbon dioxide-enriched gas from the condensable vapor-depleted waste gas stream from step (b);
   (d) chilling at least part of the separated carbon dioxide-enriched gas; and
   (e) recycling the chilled carbon dioxide-enriched gas to said reactor.

2. The process of claim 1, wherein said poly alkyl-substituted benzene is introduced into said reactor at or near its upper end and said liquid product is withdrawn from said reactor at or near its lower end.

3. The process of claim 1, wherein at least part of said carbon dioxide-enriched gas is recycled to said liquid phase.

4. The process of claim 1, wherein at least part of said carbon dioxide-enriched gas is recycled to a vapor space above said liquid phase in said reactor.

5. The process of claim 1, wherein said contacting takes place in two or more vertically-aligned liquid phase reaction zones in said reactor with oxygen-rich gas being directly introduced into at least the lowermost of said reaction zones.

6. The process of claim 5, wherein said oxygen-rich gas is directly introduced into each reaction zone.

7. The process of claim 5, wherein at least part of said carbon dioxide-enriched gas is introduced into one or more reaction zones above the lowermost reaction zone in said reactor.

8. The process of claim 5 or claim 7, wherein at least part of said carbon dioxide-enriched gas is introduced into the vapor space above the liquid phase.

9. The process of claim 1, wherein said carbon dioxide-enriched gas is formed from said waste gas stream by absorption, adsorption, condensation, oxidative reaction or combinations of these.

10. The process of claim 1, wherein said carbon dioxide-enriched gas is formed from said waste gas by adsorption.

11. The process of claim 1, wherein said carbon dioxide-enriched gas is partly formed by converting carbon monoxide in the waste gas stream to carbon dioxide.

12. The process of claim 1, wherein said oxygen-rich gas is produced in a cryogenic air separation unit.

13. The process of claim 12, wherein said carbon dioxide-enriched gas is chilled by heat exchange with oxygen-rich gas from said cryogenic air separation unit.

14. The process of claim 1, wherein vaporized saturated aliphatic acid is condensed from said waste gas and returned to said reactor.

15. The process of claim 14, further comprising withdrawing liquid reaction mixture from the lower region of said reactor, cooling the withdrawn liquid reaction mixture and returning the cooled liquid reaction mixture to said lower region of said reactor.

16. The process of claim 1, further comprising continuously stirring the liquid in said reactor.

17. The process of claim 5, further comprising continuously stirring the liquid in each of said two or more reaction zones.

18. The process of claim 1, wherein said polyalkyl-substituted benzene is a dimethyl benzene and said saturated aliphatic acid contains 2 to 6 carbon atoms.

19. The process of claim 18, wherein said dimethyl benzene acid is p-xylene, said polycarboxylic acid is terephthalic acid and said saturated aliphatic acid is acetic acid.

* * * * *